(12) United States Patent
Bracy

(10) Patent No.: US 12,220,122 B2
(45) Date of Patent: *Feb. 11, 2025

(54) MULTIPART SUTURE

(71) Applicant: Anika Therapeutics, Inc., Bedford, MA (US)

(72) Inventor: Bart Bracy, Orlando, FL (US)

(73) Assignee: ANIKA THERAPEUTICS, INC., Bedford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/487,601

(22) Filed: Oct. 16, 2023

(65) Prior Publication Data
US 2024/0115258 A1 Apr. 11, 2024

Related U.S. Application Data

(63) Continuation of application No. 15/330,819, filed on Nov. 7, 2016, now Pat. No. 11,819,207, which is a continuation of application No. PCT/US2015/029792, filed on May 7, 2015.

(60) Provisional application No. 61/989,899, filed on May 7, 2014.

(51) Int. Cl.
A61B 17/06 (2006.01)
A61B 17/00 (2006.01)
A61B 17/04 (2006.01)

(52) U.S. Cl.
CPC ........... *A61B 17/06166* (2013.01); *A61B 2017/00831* (2013.01); *A61B 2017/00964* (2013.01); *A61B 17/0401* (2013.01); *A61B 2017/0414* (2013.01); *A61B 2017/06052* (2013.01)

(58) Field of Classification Search
CPC .............. A61B 17/0401; A61B 17/06166
See application file for complete search history.

(56) References Cited

U.S. PATENT DOCUMENTS

| | | | |
|---|---|---|---|
| 2004/0010286 A1* | 1/2004 | Gieringer | A61B 17/0625 606/228 |
| 2010/0160961 A1* | 6/2010 | Nawrocki | A61B 17/06166 606/228 |
| 2013/0158598 A1* | 6/2013 | Lizardi | A61B 17/0401 606/232 |
| 2013/0238020 A1* | 9/2013 | Primavera | A61B 17/06166 606/228 |
| 2014/0081320 A1* | 3/2014 | Sengun | A61B 17/0485 606/223 |

* cited by examiner

Primary Examiner — Sarah W Aleman
(74) Attorney, Agent, or Firm — GOODWIN PROCTER LLP

(57) ABSTRACT

A multicomponent suture comprising first and second substantially elongate suture portions with respective first and second cross-sectional profiles, and further including respective first and second materials, one of said materials being bioabsorbable and a second of said materials being non-bioabsorbable.

18 Claims, 15 Drawing Sheets

MULTIPART SUTURE

CROSS-REFERENCE TO RELATED APPLICATIONS

The present application is a continuation of U.S. patent application Ser. No. 15/330,819, filed on Nov. 7, 2016, which is a continuation of PCT International patent application number PCT/US2015/029792, filed on May 7, 2015, which in turn claims benefit of U.S. provisional patent application No. 61/989,899, filed on May 7, 2014, the disclosures of all of which are herewith incorporated by reference in their entirety.

FIELD OF THE INVENTION

The present invention relates to medical fastening and more particularly to sutures and methods of suturing.

BACKGROUND

In reading the present application, the practitioner of ordinary skill in the art will appreciate that the terms "substantial" and "substantially" are intended to convey having a detectable amount and more than a negligible amount or degree of the attribute modified by the terms; the term "flexible" is intended to convey having the ability to be actively deformed and restored to its spatial condition and configuration with a minimum of persistent distortion, at least over some number of cycles, whereas the term "elastic" conveys having the characteristic of being flexible as well as having a tendency to self-restore to its original condition or configuration and, potentially, to urge other components and/or features to return to an earlier configuration. The term "elongate" is intended to convey the sense of a three dimensional object where one of the three dimensions is substantially longer than the other two dimensions.

Sutures have been used in the treatment of wounds for thousands of years. Over this time many important improvements have been made to compositions, apparatus and techniques for the use of sutures. One might think that such an extended development time would have allowed the technology to reach stasis. Nevertheless, the application of creativity and diligent effort continues to yield beneficial improvements such as those presented in the present application.

SUMMARY

Having examined and understood a range of previously available devices, the inventor of the present invention has developed a new and important understanding of the problems associated with the prior art and, out of this novel understanding, has developed new and useful solutions and improved devices, including solutions and devices yielding surprising and beneficial results.

The invention encompassing these new and useful solutions and improved devices is described below in various aspects with reference to several exemplary embodiments, including a preferred embodiment. In particular, the inventor has observed that despite long-standing efforts to provide effective surgical sutures, the available technology includes only equipment that requires suture material selection prior to insertion of the suture into the subject tissue.

Historically, sutures have been made of many different materials and it remains desirable to use a particular suture material and/or configuration in a specific application. For example, sutures are sometimes used in conjunction with fixturing devices (commonly referred to as suture anchors) that are now available for locating sutures in proximity to bone tissue so as to allow a coupling of soft tissue adjacent to the bone.

In one embodiment, the invention includes a multicomponent suture that includes a first substantially elongate suture portion with a first cross-sectional profile, where the first substantially elongate suture portion includes a first substantially bioabsorbable material. The multicomponent suture also includes a second substantially elongate suture portion with a second cross-sectional profile. The second substantially elongate suture portion includes a second substantially non-bioabsorbable material. The first and second substantially elongate suture portions are coupled to one another at respective mutually adjacent ends so as to a form an integrated suture with a first region that is substantially bioabsorbable and a second region that is substantially non-bioabsorbable.

The following description is provided to enable any person skilled in the art to make and use the disclosed inventions and sets forth the best modes presently contemplated by the inventor of carrying out his inventions. In the following description, for purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the substance disclosed. These and other advantages and features of the invention will be more readily understood in relation to the following detailed description of the invention, which is provided in conjunction with the accompanying drawings.

It should be noted that, while the various figures show respective aspects of the invention, no one figure is intended to show the entire invention. Rather, the figures together illustrate the invention in its various aspects and principles. As such, it should not be presumed that any particular figure is exclusively related to a discrete aspect or species of the invention. To the contrary, one of skill in the art would appreciate that the figures taken together reflect various embodiments exemplifying the invention.

Correspondingly, references throughout the specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout the specification are not necessarily all referring to the same embodiment. Furthermore, the particular features, structures, or characteristics may be combined in any suitable manner in one or more embodiments.

DETAILED DESCRIPTION

The following description is provided to enable any person skilled in the art to make and use the disclosed inventions and sets forth the best modes presently contemplated by the inventor of carrying out his inventions. In the following description, for purposes of explanation, numerous specific details are set forth in order to provide a thorough understanding of the invention. It will be apparent, however, to one skilled in the art that the invention may be practiced without these specific details. In other instances, well-known structures and devices are shown in schematic or block diagram form in order to avoid unnecessarily obscuring the substance disclosed.

Figure 1:
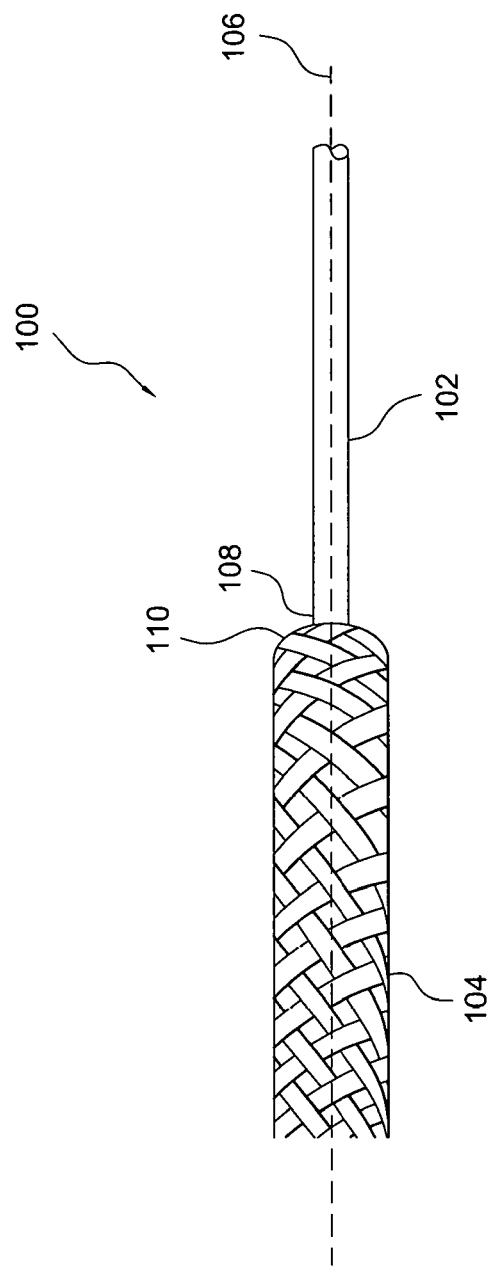
FIG. 1 shows, in schematic form, a portion of a suture prepared according to principles of the invention.

FIG. 1 shows, in schematic form, a portion of a multipart suture 100 prepared according to principles of the invention. The exemplary suture 100 includes a first monofilament portion 102 and a second braided portion 104. The first 102 and second 104 portions are generally elongate and uniform and share a common longitudinal axis 106. It will be appreciated that although the illustrated portion of longitudinal axis 106 is shown as generally linear, the first 102 and second 104 portions will typically be more or less flexible and, consequently, at any given moment, the longitudinal axis will be curved according to the instantaneous configuration of the suture portions 102, 104.

The first portion 102 is coupled to the second portion 104 at respective ends 108, 110. As will be further discussed below, this coupling will be achieved by any of a variety of coupling arrangements, according to various considerations associated with a particular anticipated application of the multipart suture 100 and with considerations of manufacturing and manufacturability.

The first 102 and second 104 portions of the suture 100 will, in certain embodiments, have a generally uniform cross-sectional profile, as taken along the longitudinal axis 106. In suture 100, as illustrated, both first 102 and second 104 portions have a generally circular cross-sectional profile. As will be further discussed below, however, a wide variety of alternative profiles will be employed in other aspects and embodiments of the invention, including embodiments in which the profile of a suture portion varies with respect to longitudinal axis 106.

Figure 2A:
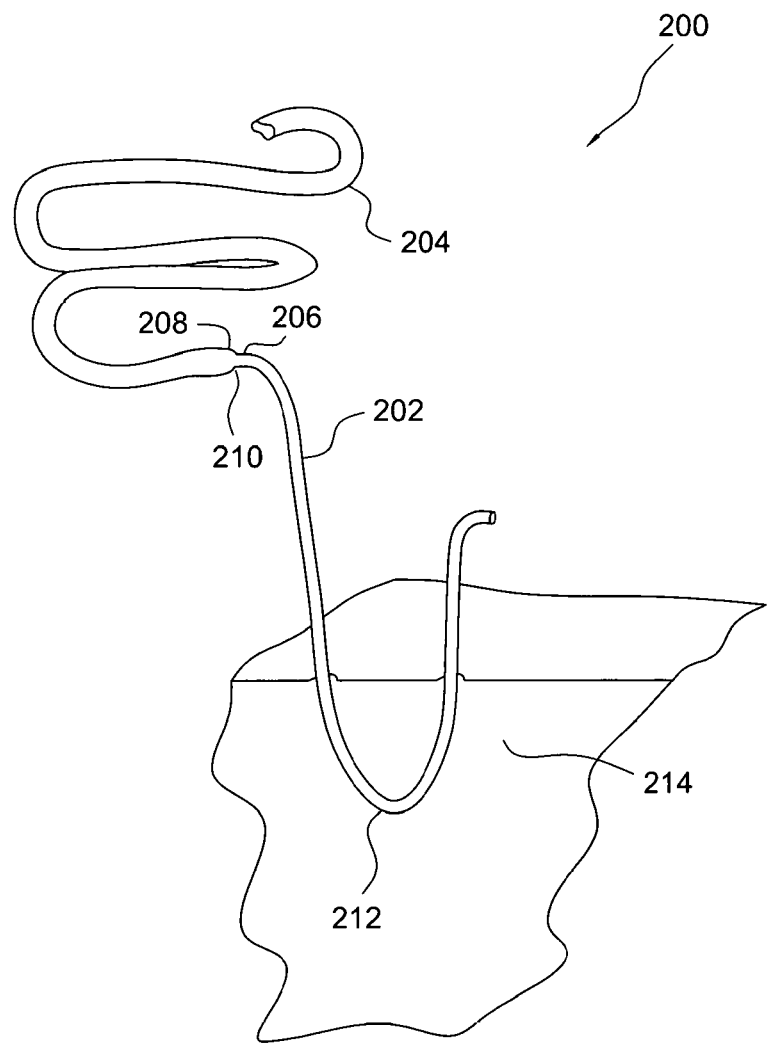
FIGS. 2a-2C show respectively, in schematic form, a portion of a suture prepared according to principles of the application in various states or stages of application, and illustrate a method according to the same.
Figure 2B:
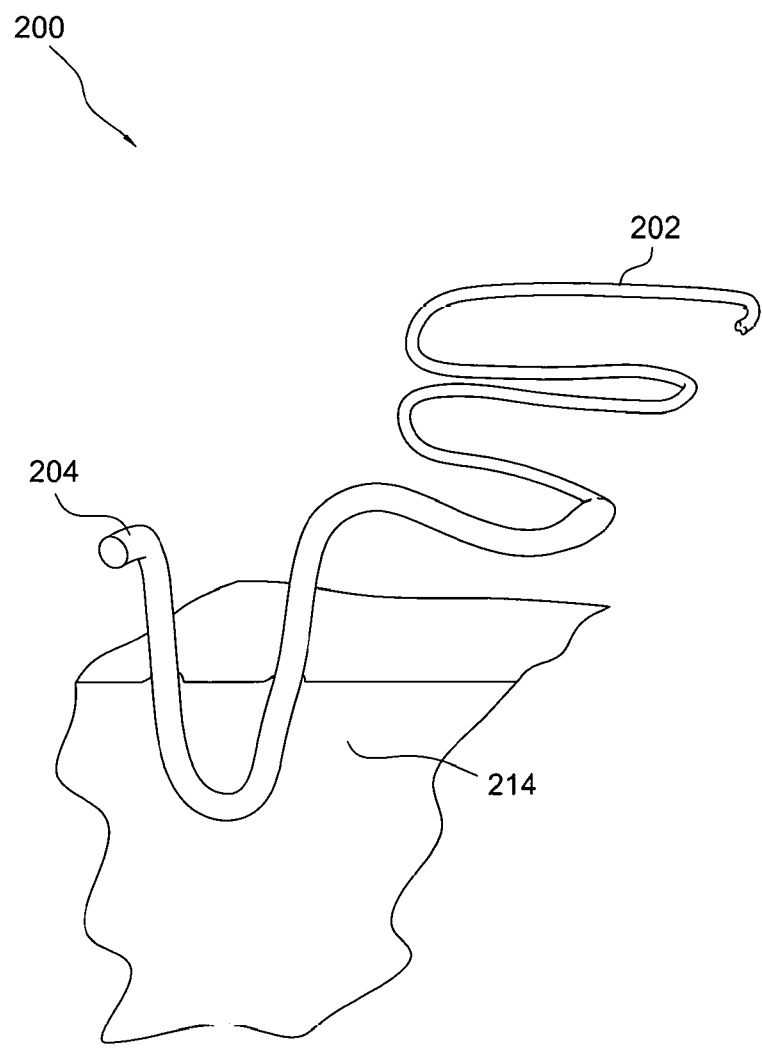
Figure 2C:
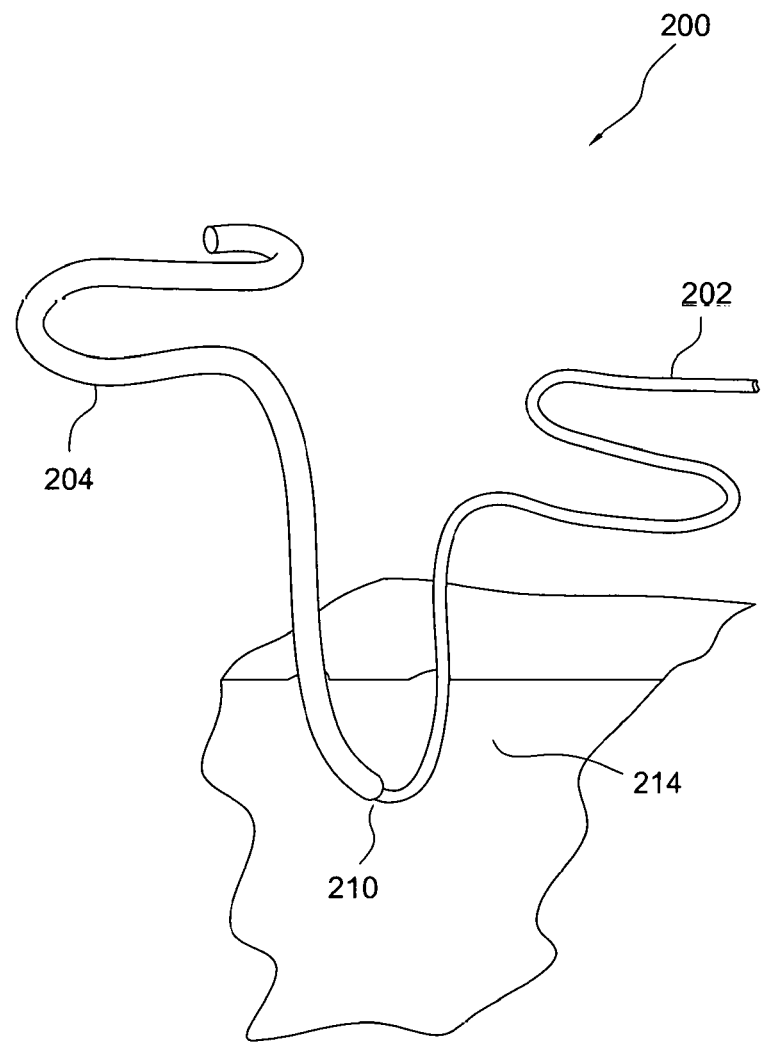

FIGS. 2A, 2B and 2C illustrate schematically certain attributes of a multicomponent suture 200 prepared according to principles of the invention when in use. FIG. 2A shows a suture 200 having first 202 and second 204 longitudinal portions. The first and second portions are coupled to one another at respective adjacent ends thereof 206, 208 at a coupling region 210 of the suture. In the illustrated exemplary application, part 212 of first longitudinal portion 202 is disposed within a tissue matrix 214.

It will be appreciated that the tissue matrix may be any of a wide variety of materials including, for example and without limitation, muscle, bone, tendon, ligament, and any organ including, again without limitation, skin, eye, kidney, heart, brain, lung, spleen, etc. it will also be appreciated that the tissue matrix may be human or otherwise, and that a suture according to principles of the invention will be used in medical applications, veterinary applications and other applications limited only by the imagination of the user. The part 212 of first longitudinal portion 202 will have been disposed within the tissue matrix 214 by any appropriate method or apparatus including without limitation, by coupling a region of the longitudinal portion 202 to a needle (not shown) and using the needle in a conventional manner to draw the first longitudinal portion 202 into and through the tissue matrix 214.

Having achieved the illustrated configuration, a user can elect to cut off and discard the second portion 204 of the suture, proceeding thereafter to use the first portion 202 of the suture in any conventional manner. Alternately, the user can draw the suture 200 through the tissue matrix 214 so as to achieve the configuration illustrated in FIG. 2B. Thereafter, the user can elect to cut off and discard the first portion 202 of the suture, proceeding thereafter to use the second portion of the suture 204 in any conventional manner. As yet another alternative, the user can elect to draw suture 200 through the tissue matrix 214 until the coupling region 210 is within the tissue matrix 214, as illustrated in FIG. 2C. Thereafter, the user can use any part of the first 202 and second 204 portions of the suture 200 in whatever manner is deemed by the user to be beneficial.

In regarding the suture 200, and its method of use, as exemplified in FIGS. 2A-2C it will become evident to the creative practitioner of ordinary skill in the art that a suture according to principles of the invention has the great advantage of allowing the user to select for use, in particular circumstances, the portion of the suture having characteristics most suitable to those circumstances. Thus, for example, rather than having to identify, in advance of deployment, the suture characteristic that will be most beneficial to a particular circumstance, the user can identify those characteristics at the moment of deployment and adjust the suture accordingly.

The attributes of the suture of the invention will exhibit particular advantages in circumstances such as, for example, use by a paramedic or a combat medic. For such a user, access to an inventory of different sutures having different characteristics, while desirable, can be highly problematic. Moreover, selection of suture characteristics may be rendered difficult by the exigent circumstances (e.g., combat, natural disaster, fire, wilderness first aid and rescue, etc.). In such circumstances, the ability to carry a single suture exhibiting multiple characteristics can be greatly beneficial.

It should be understood, however, that the same characteristics can be similarly beneficial in the operating theater. Often, the surgeon or other medical professional will be faced with circumstances that evolve during the course of an operation or other therapeutic procedure. The ability to select desired characteristics of a suture in real time simply by drawing the suture more or less completely through a tissue penetration can ease decision-making in an otherwise highly stressful environment. Moreover, in some circumstances, the ability to modify the characteristics of the suture in use as circumstances evolve will avoid the need to withdraw one suture after it has been inserted and replace it with another. This can reduce the time necessary for the procedure and, potentially, the number of personnel required to assist.

It will be appreciated that, in appropriate circumstances, all of these benefits of the present invention will tend to save time in the course of a procedure and facilitate a beneficial outcome. Notwithstanding that anesthesia has improved vastly in recent years, every surgical procedure retains some level of risk, and the ability to operate efficiently and quickly remains of great advantage to the likelihood of a successful outcome and, thus, to the ultimate interest of the patient.

Referring again to FIG. 1, and as previously noted, the suture 100 includes a first portion 102 shown as a monofilament suture portion and a second portion 104 shown as a braided suture portion. It should be understood that these are merely illustrative of characteristics that will be incorporated in suture portions of respective embodiments of the invention. Thus, for example, in certain embodiments, the monofilament portion 102 will include a bioabsorbable material and the braided portion 104 will include a non-bioabsorbable material. Thus, consistent with the discussion above of suture 200 in relation to FIGS. 2A-2C, a user can select for application in a particular circumstance, a bioabsorbable or a non-bioabsorbable suture simply by drawing the suture more or less completely through the tissue matrix.

It will be further understood that, in certain embodiments (and conversely to the example above), a braided portion of the suture will include a bioabsorbable material while the monofilament portion of the suture will include a non-bioabsorbable material. Further, and as exemplified in FIG. 3, in certain embodiments a single suture will incorporate more than two portions, where different physical configurations and different levels of bioabsorbability will be exhibited by the respective portions.

Figure 3:
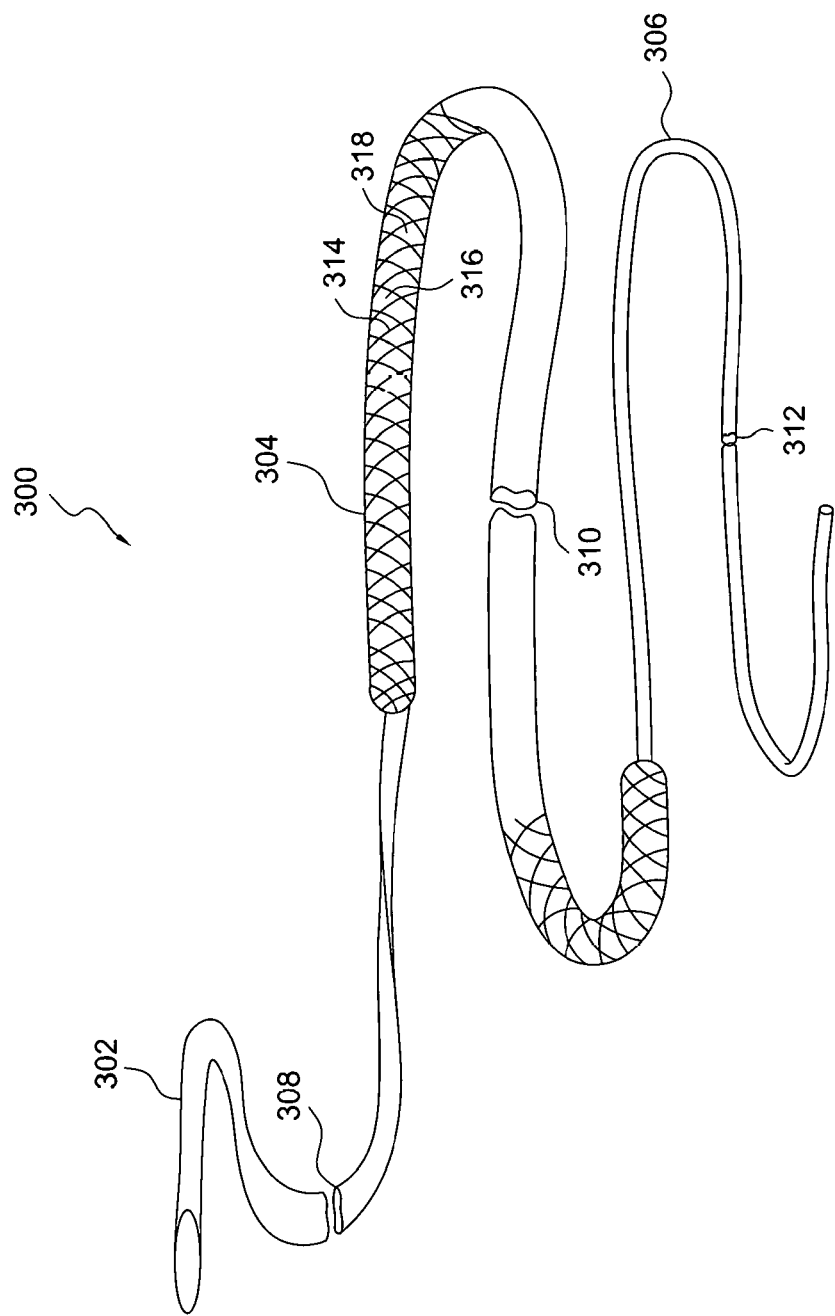
FIG. 3 shows, in schematic form, a portion of a suture including three components, prepared according to principles of the invention.

FIG. 3 thus illustrates a suture 300 including a first portion 302, second portion 304, and a third portion 306. Each of portions 302, 304 and 306 has a different physical and/or chemical characteristic and may be selected for use as described above. Thus, for example, in certain embodiments first portion 302 will be a bioabsorbable monofilament having a first relatively short time constant for bioabsorption, second portion 304 will be a substantially non-bioabsorbable woven suture and third portion 306 will be a bioabsorbable monofilament having a second relatively long time constant for bioabsorption. Moreover, while the cross-sectional profile of the first, second and third portions will, in certain embodiments be similar to one another (as, for example, all substantially circular) in the illustrated suture 300, illustrative cutaways show that the cross-sectional profile 308 of first portion 302 is flattened, or elliptical, as compared with the substantially circular cross-sectional profile 310 of second portion 304 and the likewise substantially circular cross-sectional profile 312 of third portion 306.

In certain embodiment of the invention, it will be beneficial to color code a particular portion of a suture so as to readily identified to a user the characteristics of that portion of the suture. Thus, for example, in certain embodiments a monofilament portion such as portion 302 will include a dye within this formulation producing a uniform and identifiable color at its surface. In other embodiments, a colored coating will be applied to an external surface of the suture material. In still further embodiments, a colored material will be disposed internally within the suture (as, for example, by co-extrusion) and be visible through a transparent or translucent outer material of the suture. Still further, a woven suture such as that of portion 304 will include, in respective embodiments, one or more fibers (e.g., 314, 316, 318) exhibiting one or more respective colors, where the color is the result of an intrinsic component material, a coating, or a co-extruded internal portion, etc., as discussed above.

It will be appreciated by one of ordinary skill in the art that in addition to coloration, patterns and patterns of colors will be provided in respective embodiments to identify particular suture portions and characteristics of suture portions. Such patterns will be applied by any appropriate method, such as is known or becomes known, including, for example and without limitation, material dying, printing, painting, dipping, bleaching, laser marking including chemical activation, ablation, bleaching, and burning. In certain embodiments, the identifying pattern will consist of readable symbols including numbers, letters, other characters, and machine-readable markings including barcodes and other machine-readable codes.

In still further embodiments, surface markings and/or surface texture will be employed to help a user readily identify the characteristics of a particular portion of the suture. Thus, for example, the characteristics of a particular portion of a suture will be apparent to a user based on the sense of touch, even where the portion of the suture in question is obscured by its placement within a wound or a body cavity, by the absence of light in an emergency or first aid situation, or by other factors. A surface marking or surface texture will be included on a portion of a suture either as a result of an intrinsic characteristic of the suture portion (as, for example the difference between a woven, knitted or braided portion and extruded monofilament or multifilament portion) or as a result of an active manufacturing step. Thus, in certain embodiment, manufacturing of a portion of a suture will include embossing, grooving, cutting, laser marking, rolling, or any other process appropriate to make a portion of a suture identifiable by touch. It should be recognized that along with other benefits, a particular cross-sectional profile will aid in the identification of a particular portion of a suture to a user.

Figure 4A:
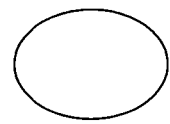
FIGS. 4A-4P each show, in schematic form, a respective cross-sectional profile of a respective suture prepared according to principles of the invention.
Figure 4G:
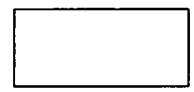
Figure 4L:
Figure 4B:
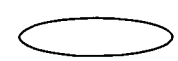
Figure 4H:
Figure 4M:
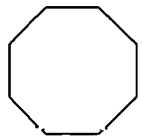

As noted above, different embodiments and aspects of the invention will include different cross-sectional profiles associated with one or more portions of a suture. FIGS. 4A-4P illustrate, in schematic form and purely for exemplary purposes, various cross-sectional profile that will be beneficially applied in respective embodiments of the invention.

Accordingly, FIG. 4A shows a cross-section of a portion of a suture having a generally elliptical profile; FIG. 4B shows a cross-section of a portion of a suture having a further elliptical profile with a larger differential between the horizontal and vertical axes (as compared with that of FIG. 4A) so as to present a flattened aspect like that of a ribbon or tape. It will be understood that the ratio between the horizontal and vertical axes of the cross-sectional profile are referred to as an aspect ratio of the cross-sectional profile. In various embodiments of the invention, a suture portion will include a cross-sectional profile having an aspect ratio of between, for example 0.001 (1/1000) and 1 (one or unity).

More commonly, a suture portion will include a cross-sectional profile have an aspect ratio of between 0.1 (1/100) and one. Typically, the aspect ratio of a suture portion will be substantially constant as a function of position along the longitudinal axis of the suture portion. In some embodiments, however, the aspect ratio will vary as a function of location along the suture portion.

Figure 4C:
Figure 4I:
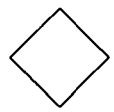
Figure 4N:
Figure 4D:
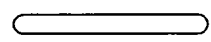
Figure 4J:
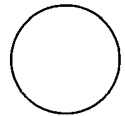

FIG. 4C show the cross-sectional portion of the suture having a flat-oval profile with first and second substantially linear regions and, disposed therebetween, semicircular regions again, giving more or less the impression of a ribbon or tape; this tape-like characteristic is further apparent the suture portion profile presented in FIG. 4D which again has a generally flat-oval characteristic; 4E illustrates a suture portion having an arcuate tape profile where, in various embodiments, the arc will reflect a circular arc, an elliptical arc, or any other arc appropriate to a particular application; FIG. 4F again shows a generally tape-like cross-sectional profile, here incorporating a reverse curve. It will be appreciated that any complex curve including, for example, multiple reverse curve, will be employed in appropriate embodiments of the invention. Other suture portion profiles intended to fall within the scope of the invention include the rectangular profile of 4G; the flattened rectangular profile (again a tape or ribbon style profile) of 4H; a square or diamond-shaped profile as in FIG. 4I; a substantially circular profile as in FIG. 4J and as discussed above; or a tubular profile as illustrated by the square tubular profile of FIG. 4K.

It will be appreciated that in the case of a tubular profile, an internal region of the suture portion may be evacuated, or may be open to the ambient atmosphere, or may contain a solid or liquid or gaseous material having characteristics that make the overall characteristics of the suture portion desirable. In like fashion, the internal region 402 of the tubular suture portion may form the structural portion of the apparatus, while the exterior of the tubular suture portion 404 may have other beneficial characteristics including desirable lubricity, desirable optical characteristics, desirable texture, desirable biocompatibility, or any other desirable characteristic.

FIG. 4P shows a further cross-section of a suture portion, here substantially circular and tubular (i.e., circular cylindrical) where all of the various considerations discussed above in relation to the square tubular will likewise apply in respective embodiments and aspects of the invention. Of course it will be appreciated that in addition to square and circular tubular configurations, other geometrical configurations will be beneficially employed in respective applications of the invention.

Figure 4O:
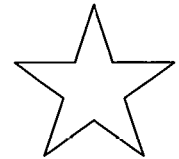
Figure 4E:
Figure 4K:
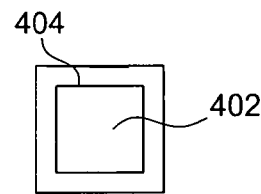
Figure 4P:
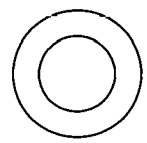
Figure 4F:

FIG. 4L shows a hexagonal cross-section of a corresponding suture portion; 4M shows an octagonal cross-section of a corresponding suture portion; 4N shows a triangular cross-section of a corresponding suture portion; FIG. 4O shows a stellate cross-section of a corresponding suture portion. Again, it should be emphasized that these various geometrical configurations disclosed here are not intended to form an extensive list, but are merely exemplary of the wide variety of cross-sectional profile that will be beneficially employed and readily apparent to one of ordinary skill in the art who considers the matter in light of the foregoing disclosure.

It will be appreciated, of course, that any other profile appropriate to a particular application of the invention will be beneficially applied to a respective portion of a suture, and that such application is considered to fall within the scope of the invention, and to be proprietary to the extent that it is ultimately claimed.

Figure 5A:
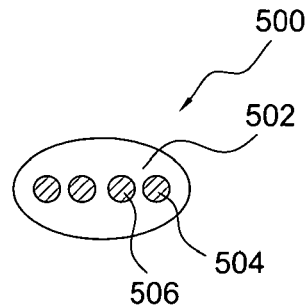
FIGS. 5A-5E each show, in schematic form, a respective cross-section of a portion of a respective suture prepared according to principles of the invention.

FIGS. 5A-5E illustrate further aspects of the invention, according to which reinforcing materials are disposed within one or more portions of a suture prepared according to principles of the invention. Thus, FIG. 5A shows, in cross-section, a portion of a suture 500 according to principles of invention, the cross-section having a generally ribbon elliptical configuration where a first material 502 surrounds and encapsulates a plurality of generally really flexible longitudinal members, e.g., 504, 506 of generally circular cross-section.

In one exemplary embodiment, the generally flexible longitudinal members 504, 506 will be selected for their tensile characteristics, while the surrounding material 502 provides a desirable cushioning characteristic, a desirable degree of biochemical imperviousness, or other desirable characteristic. It should be understood that in other embodiments, the external material 502 may be selected for its tensile properties while the internal material 504, 506, etc. will have other beneficial characteristics.

Figure 5B:
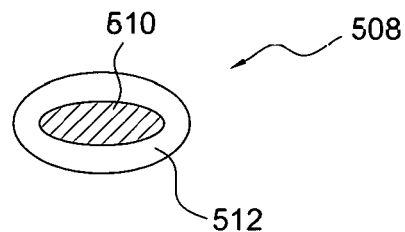

FIG. 5B shows, in cross-section, a further suture portion embodiment 508 of similarly generally elliptical configuration, again with an internal portion 510 and an external portion 512. As with the embodiment described above, the characteristics of the internal portion 510 and the external portion 512 will differ and be selected to complement one another. Thus, for example, the internal portion 510 may have desirable tensile characteristics while the external portion 512 may have other desirable physical properties.

Figure 5C:
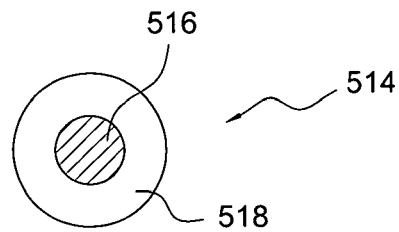
Figure 5D:
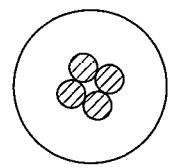
Figure 5E:
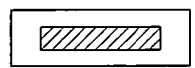

FIG. 5C shows a still further portion of an embodiment 514 of generally circular configuration. Once again, the characteristics of the internal portion 516 and the external portion 518 will differ and be selected to complement one another. Thus, for example, the internal portion 516 may have desirable tensile characteristics while the external portion 518 may have other desirable physical properties. Likewise, FIGS. 5D and 5E illustrate exemplary arrangements and embodiments with characteristics that are self-evident in light of the figures themselves and the foregoing explanation.

Referring again to FIG. 5C, it should be noted that, in certain embodiments and aspects of the invention, one or the other of the internal portion 516 and the external portion 518 will be bioabsorbable while the other will not be. Alternately, the two portions 516, 518 may both be bioabsorbable, but with different bioabsorption time constants such that one is absorbed more rapidly than the other. Thus, a particular application of the suture can be engineered to provide varying characteristics over the in vivo life of the suture.

Purely as an example, external material 518 will be chosen, in certain embodiments, to be substantially less elastic than internal material 516 and also external material 518 will be chosen to have a substantially shorter bioabsorption time constant than internal material 516. Consequently, after being deposited in vivo, during a first time period the suture will have a first relatively inelastic characteristic. Upon the more or less complete absorption of the external material 518, however, the characteristics of the internal material will come to dominate the structure such that the overall elasticity of the suture become higher than it was at installation; i.e., the suture as a whole becomes more elastic with time.

Figure 6:
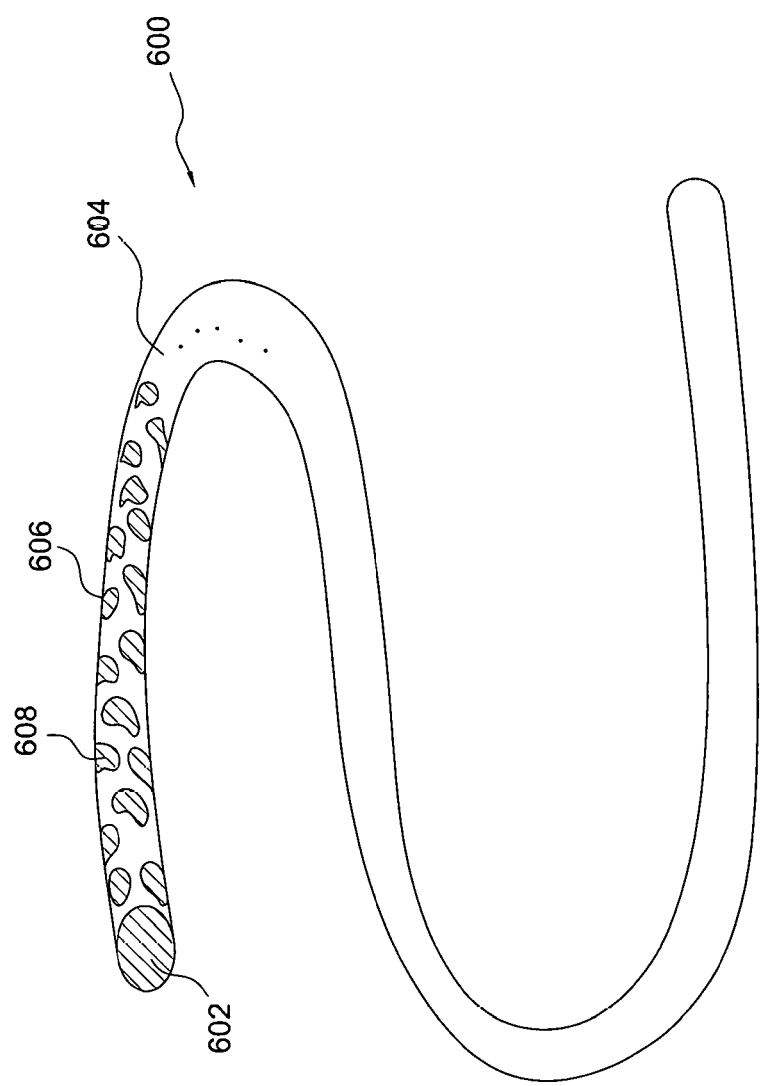
FIG. 6 shows, in schematic form, a portion of a suture prepared according to principles of the invention.

FIG. 6 shows a portion 600 of a further suture embodiment according to principles of the invention. As discussed above, suture portion 600 includes an internal material 602 and an external material 604 having different respective characteristics. In the illustrated embodiment, the external material includes a plurality of preparations, e.g., 606, such that certain regions 608 of the internal material 602 are exposed.

As with the embodiments discussed above, the materials of suture portion 600 will be selected, in certain embodiments, to have different time constants for bioabsorption. In certain embodiments, the internal material 602 will have a shorter bioabsorption time constant then the external material 604. Consequently, the suture portion 600 can be arranged such that as the internal material 602 is absorbed, the overall assembly of suture portion 600 becomes more flexible and/or elastic.

The bioabsorption time constant of the external suture material 604 will, in certain embodiments, be substantially indefinite, such that the extra material remains behind substantially permanently after the internal material dissolves. As such it will be understood that while the discussion of FIG. 1 involves selecting one portion of the multi-part suture while removing and discarding another portion, it is also within the scope of the invention to prepare an employee multipart suture were more than one part of the suture is used, and where different parts of the suture may be co-located. In certain embodiments, the different parts will have different characteristics including different markings, different chemical and physical properties, and different levels of persistence when applied in vivo.

Again, referring to FIG. 1, where two portions 102, 104 of a suture are coupled together, various coupling means will be employed in respective embodiments of the invention. In some embodiments, where the configuration or structure of the two portions 102, 104 differ but the materials of the two portions 102, are identical or substantially similar, the two portions may be formed integrally without any discrete coupling mechanism. In other embodiments, as discussed below, various coupling mechanisms appropriate to the particular circumstances and as known in the art or as will be discovered, are employed. Examples follow, on the basis of which the practitioner skilled in the art will understand further principles of the invention, and readily arrive at many additional and derivative arrangements and embodiments.

Figure 7:
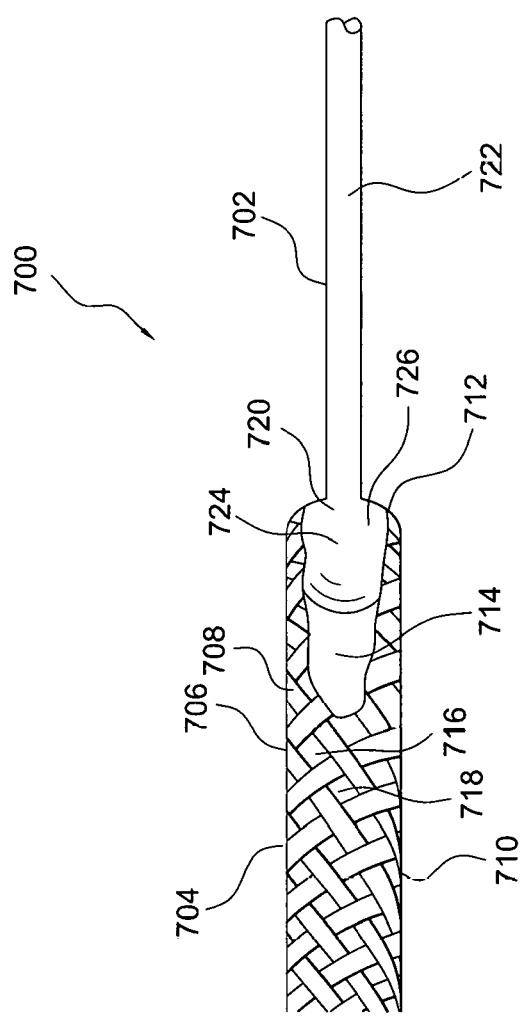
FIG. 7 shows, in schematic cutaway form, a coupling portion of a suture prepared according to principles of the invention.

FIG. 7 shows, in cutaway schematic view, a portion of an exemplary suture 700 prepared according to principles of the invention. The exemplary suture 700 includes a first monofilament portion 702 and a second braided portion 704. The first 702 and second 704 portions are generally elongate and share a common longitudinal axis (not shown). In the illustrated example, braided portion 704 includes a plurality of fibers, threads or yarns e.g., 706, 708 arranged and configured to form a generally tubular portion 710 and a substantially closed-end referred to as a sock toe portion 712.

Like the toe of a sock, the closed-end sock toe portion 712 terminates the tubular portion and serves to close one end of an internal cavity 714 defined within the tubular portion 710. In the illustrated embodiment, the fibers, threads or yarns exemplified by 706 and 708 define apertures therebetween, e.g. 716, 718. Similar apertures are present in the sock toe portion 712 and, in the illustrated embodiment, a region of the second monofilament portion 702 is disposed within one such aperture, such that part 720 of monofilament portion 702 is disposed within cavity 714 and another part 722 of monofilament portion 702 is disposed outside of cavity 714.

As illustrated, the part 720 of monofilament 702 disposed within cavity 714 includes an enlarged portion 724. In the illustrated embodiment, this enlarged portion 724 embodies a generally spherical aspect, having a peripheral surface region 726 arranged and adapted to interfere mechanically with fibers of the sock toe region and effectively couple the first monofilament portion 702 and second braided portion 704 of the exemplary suture 700 substantially coherently to one another.

It will be appreciated by one of skill in the art that the flexible nature of the braided fibers, threads or yarns, along with the arcuate spherical shape of the peripheral surface region 726 will allow flexibility at the joint so that a longitudinal axis of the first monofilament portion 702 can pivot somewhat freely with respect to a longitudinal axis of the second braided portion 704.

It will be further understood that enlarged portion 724 need not be spherical, but may include arty of a wide variety of forms appropriate to particular circumstances. Moreover, enlarged portion 724 may be integrally formed as part of the monofilament portion 722 (e.g., be molded or extruded in place or formed by plastic deformation with or without reheating), or may be a separate element or component coupled to the balance of first monofilament portion 722 by any appropriate method. Thus, in various embodiments, the enlarged portion 724 and the balance of the monofilament portion 722 will be coupled by the application of one or more of a combination of internal and external threads, respectively, thermal welding, ultrasonic welding, chemical adhesion, physical pressfit/friction fit, swaging, riveting, the use of a fastener such as a nail, a screw, a bolt, a roll pin, a cotter pin, or any other fastening means which is or becomes known to those of skill in the art.

Figure 8:
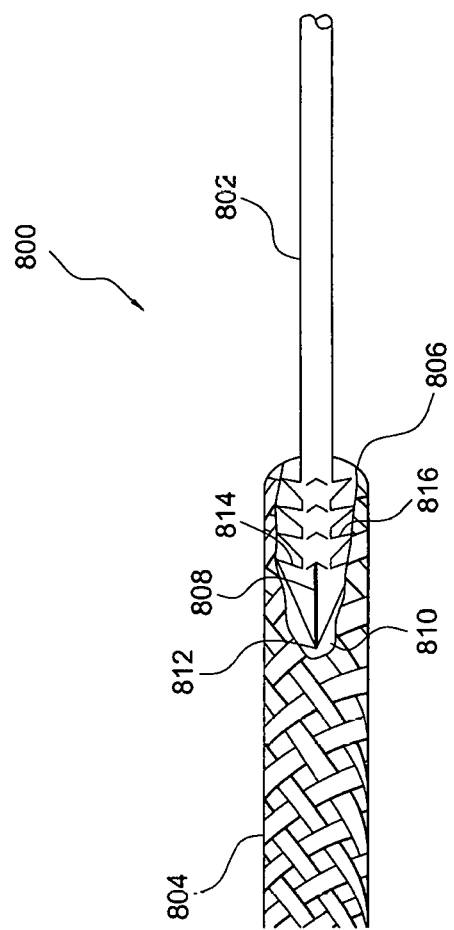
FIG. 8 shows, in schematic cutaway form, a coupling portion of a suture prepared according to principles of the invention.

FIG. 8 shows, in cutaway schematic view, a portion of a further exemplary suture 800 prepared according to principles of the invention. The exemplary suture 800 includes a first monofilament portion 802 and a second braided portion 804. The second braided portion 804 includes a sock toe region 806. A portion of monofilament portion 802 is disposed through an aperture between fibers of the sock toe region 806, and an enlarged portion 808 of monofilament portion 802 is disposed within a cavity 810 defined within the braided portion 804.

In the illustrated embodiment, the enlarged portion 808 is configured to include a pointed end 812 and a plurality of barbs, e.g., 814, 816. The pointed end 812 facilitates insertion of the enlarged portion 808 into and through the aperture between fibers of the sock toe region 806 during manufacturing (or otherwise prior to application) of the suture 800. The barbs, e.g. 814, 816 include their own respective points which tend to pass into fibers, threads or yarns of the braided portion 804 and/or into other apertures between those fibers, thereby preventing this engagement of the first monofilament portion 802 from the second braided portion 804.

As with the generally spherical enlarged portion 724 described above with respect to FIG. 7 the barbed enlarged portion 808 of the present embodiment will be, in certain embodiments, integrally formed with the monofilament portion 802, or may be a separate element or component coupled to the balance of monofilament portion 802 by any of the means and methods discussed above. Likewise, it may be formed of any appropriate material including, for example, nylon, stainless steel, titanium, ultrahigh molecular weight polyethylene, polytetrafluoroethylene, gold, or any other appropriate material, bioabsorbable or non-bioabsorbable according to the requirements of the particular application.

Figure 9:
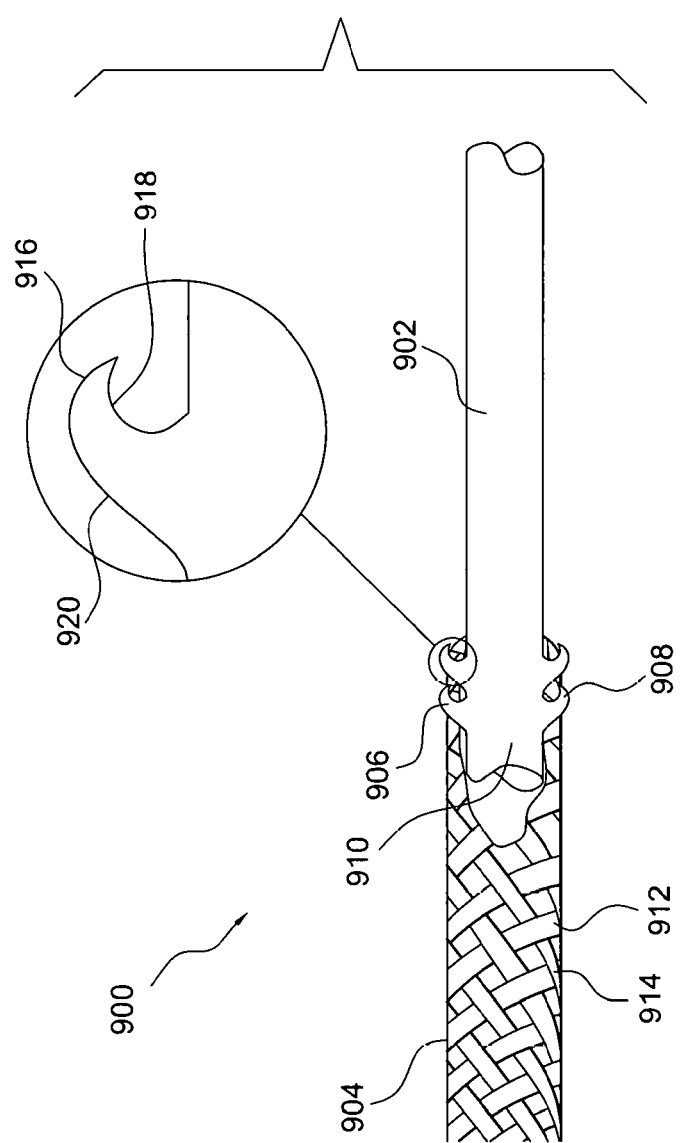
FIG. 9 shows, in schematic cutaway form, a coupling portion of a suture prepared according to principles of the invention.

FIG. 9 shows, in cutaway schematic view, a portion of a further exemplary suture 900 prepared according to principles of the invention. The illustrated embodiment includes a monofilament portion 902 and a braided portion 904. A plurality of barbed features 906, 908 are disposed adjacent a proximal end 910 of the monofilament portion 902. Consistent with the foregoing description, the barbed features 906, 908 are adapted to pass through apertures between fibers, threads or yarns, e.g. 912, 914 of the braided portion 904.

In certain embodiments, the barbed features include an arcuate distal end 916 having a generally concave inner surface region 918 well adapted to interfere with and couple to the fibers, threads or yarns of the braided portion 904, and a generally convex outer surface region well adapted to minimize interference of the barbed portion with features of the environment including a destination tissue matrix.

In certain embodiments of the invention, the barbed features 906, 908 initially lack the arcuate surfaces 918, 920. During manufacturing of the suture 900, physical forces are applied to deform the barbed features 906, 908 so that their surfaces assume the subject arcuate configuration and effectively locking the barbed features to the fibers, threads or yarns of the braided portion 904.

Figure 10:
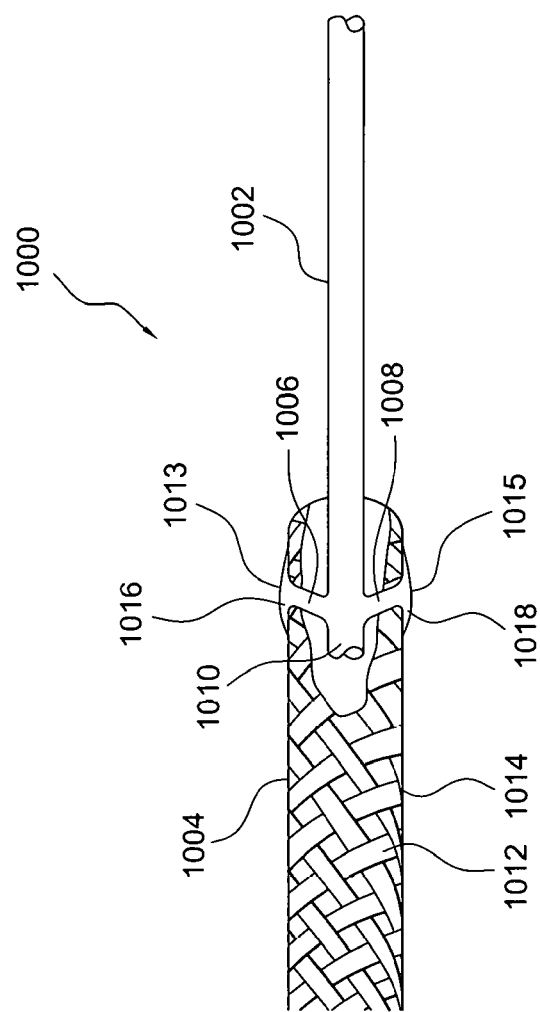
FIG. 10 shows, in schematic cutaway form, a coupling portion of a suture prepared according to principles of the invention.

FIG. 10 shows, in cutaway schematic view, a portion of a still further exemplary suture 1000 prepared according to principles of the invention. The illustrated embodiment includes a monofilament portion 1002 and a braided portion 1004. A plurality of barbed features 1006, 1008 are disposed adjacent a proximal end 1010 of the monofilament portion 1002. Consistent with the foregoing description, the barbed features 1006, 1008 are adapted to pass through apertures between fibers, threads or yarns, e.g. 1012, 1014 of the braided portion 1004. In the illustrated embodiment, the respective ends 1013, 1015 of the barbed features are deformed after passing through the apertures so as to more effectively couple the monofilament portion 1002 to the braided portion 1004.

In certain embodiments, this deformation of the ends 1012, 1014 is a plastic deformation achieved with or without thermal heating of the barbed features 1006, 1008. Thus in certain embodiments, the ends 1012, 1014 are deformed by convective thermal heating, by radiative thermal heating, by conductive thermal heating, by laser heating, by microwave heating, by frictional heating, by compressive heating, or without any heating at all. Again, in certain embodiments, the deformation process is arranged and adapted to produce on an external surface 1016, 1018 of each barb 1006, 1008 respectively, a substantially smooth surface region well adapted to avoid unwanted interference with a tissue matrix and any other environmental features during installation of the suture 1000.

Figure 11:
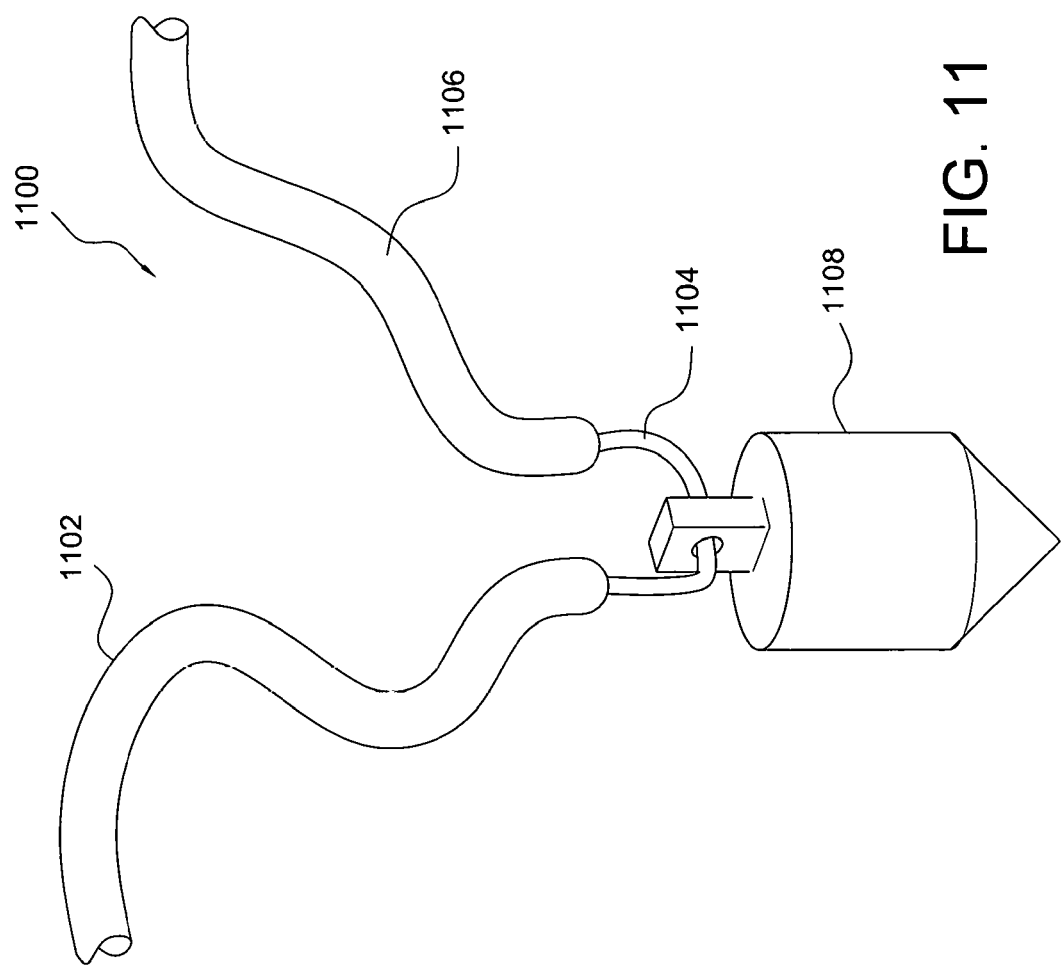
FIG. 11 shows, in schematic form, a portion of a suture prepared according to principles of the invention including a suture anchor portion.

FIG. 11 shows, in schematic view, a further aspect of the invention in which a multipart suture assembly 1100 includes first 1102, second 1104 and third 1106 suture portions, as well as, for example, a suture anchor portion 1108. It should be appreciated that the suture anchor illustrated displays only general schematic features and may represent any of a wide variety of suture anchors.

The suture portion 1104 is adapted by physical configuration and selection of materials to be well adapted to provide a substantial and reliable interface to the suture anchor portion 1108. Likewise the suture portions 1102 and 1106 are similarly adapted by physical configuration and selection of materials to be well adapted to provide a substantial and reliable interface to, for example a soft tissue matrix. It will be appreciated that the suture coupling methods described above will be effectively employed in the preparation of a multipart suture assembly like that of suture assembly 1100.

Figure 12:
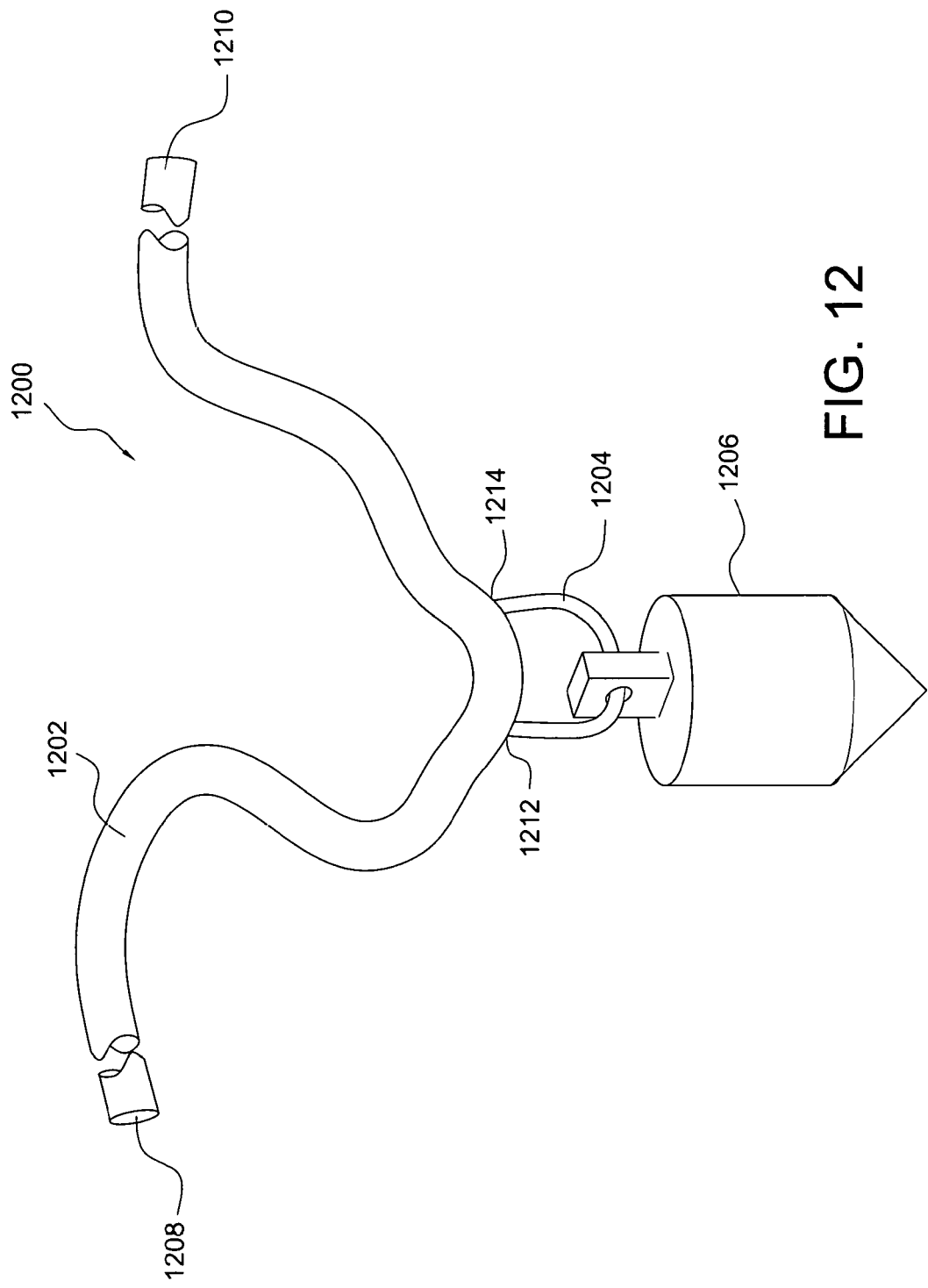
FIG. 12 shows, in schematic form, a portion of a suture prepared according to principles of the invention including a suture anchor portion.

FIG. 12 shows, in schematic view, a further aspect of the invention in which a multipart suture assembly 1200 includes first 1202 and second 1204 suture portions as well as a suture anchor portion 1206. As illustrated, the first suture portion 1202 is substantially continuous from a first end 1208 to a second end 1210. At intermediate points 1212, 1214 of the first suture portion 1202, respective ends of the second suture portion 1204 are coupled to the first suture portion, forming a loop including suture portion 1204. The loop of suture portion 1204 is coupled to the suture anchor portion 1206 as indicated. It will be appreciated by one of skill in the art that the coupling between the ends of the second suture portion 1204 and the first suture portion 1202 will be achieved, in certain embodiments, using barbed features or other apparatus similar to that described above.

In certain embodiments, the materials of suture portion 1202 and suture portion 1204 will be selected such that the bioabsorption time constant of the second suture portion 1204 will be substantially shorter than that of the first suture portion 1202 (and in some cases the first suture portion 1202 will be non-bioabsorbable). Consequently, after a period of time determined by the characteristics of the material of the second suture portion 1204, the suture 1200 will become detached from the suture anchor while retaining its relation to, for example, soft tissue in which the suture portion 1202 is disposed. As a result, the multipart suture assembly 1200 is well adapted to provide a temporary stabilization of soft tissue by attaching it to, for example, adjacent bone tissue matrix, during initial healing. Thereafter, when the same level of stabilization is no longer required, the soft tissue is released from the bone by bioabsorption of suture portion 1204, but remains supported by the suture portion 1202.

Figure 13:
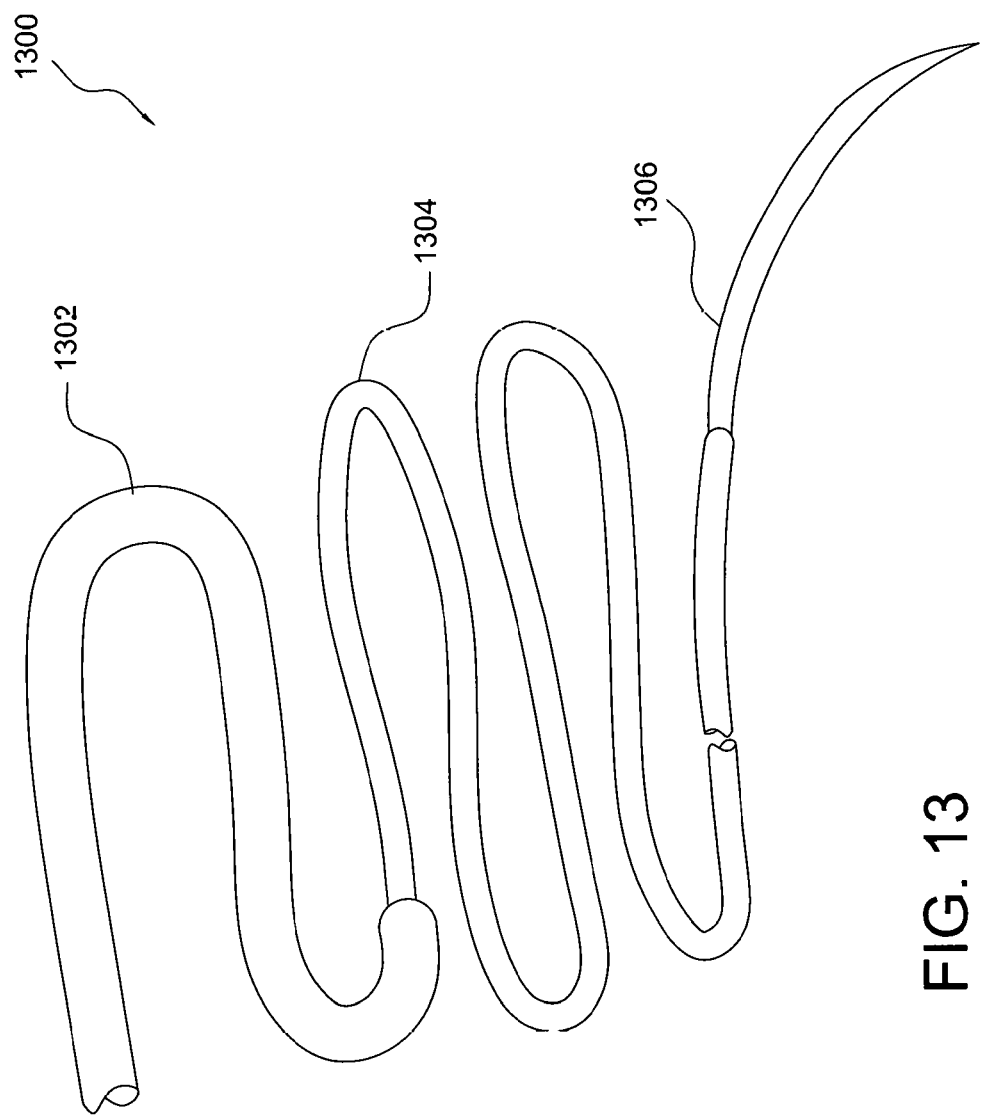
FIG. 13 shows, in schematic form, a portion of a suture prepared according to principles of the invention including a needle portion.

FIG. 13 shows a further aspect of the invention in which a multipart suture 1300, similar to that shown in FIG. 1, is provided as part of a kit or integrated unit including a first suture portion 1302, a second suture portion 1304 and an integrated needle 1306.

A variety of general considerations relating to any and all of the foregoing disclosure is now reviewed. It will be understood by one of skill in the art that the foregoing references to bioabsorbable and non-bioabsorbable materials are intended to cover any bioabsorbable and non-bioabsorbable materials respectively as known in the art, as well as additional material that may become known with the further development of the technology. Thus the term bioabsorbable materials intended to include, without limitation materials such as polydioxanone (PDS), polyglycolic acid (PGA), polylactic acid (PLA), copolymers including the (L/D) LA copolymers which are a mixture of D- and L-isomers of PLA, PLGA copolymers which include a combination of PLA and PGA and self-reinforcing materials including a competent structure made from partially crystalline/amorphous material of oriented fibers/fibrils and a binding matrix. In summary: SR PLLA; PLLA; P (D/L) LA 70/30; PLA/PGA (PLGA) 80/20; SR PGA; PDA: and PGA.

In certain embodiments, the multicomponent suture will include a braided ultrahigh molecular weight (UHMW) polyethylene or polyester suture coupled at one end to a corresponding end of a monofilament of absorbable or nylon suture. In other embodiments, a suture prepared according to principles of the invention will include a polyvinylidene fluoride (PVDF) material (known commercially as Kynar™), and in still other embodiments a suture prepared according to principles of the invention will include a polytetrafluoroethylene (PTFE) (known commercially as Teflon™). In still other embodiments, a suture prepared according to principles of the invention will include a metallic material such as, for example, stainless steel, titanium and gold. It will be appreciated that a particular embodiments of the invention may include any combination of the foregoing, as well as any other material known in the art, or which becomes known in the art to be useful with respect to the present technology. In addition, perforated and expanded materials will find application with any or all of the above-described embodiments.

Beyond this, it will be understood that while several exemplary methods have been described above for the coupling of first and second suture portions, a wide variety of other coupling methods will be applicable to the present invention, and are intended to fall within the scope of the present disclosure. Thus, for example, chemical adhesives types and forms will be beneficially applied. For example, a cyanoacrylate based adhesive will be advantageously applied in certain embodiments. It should be noted that, in instances where one or the other portion of the suture is to be detached and removed (i.e. not left within the patient) it will, in certain embodiments, be desirable to use a non-biocompatible adhesive or other material in the portion that is intended to be removed.

It should be noted that the coupling between suture portions will be effected in certain embodiments with a thermally bonded joint; an ultrasonically welded joint; an integrally molded joint; preloaded (with the end of the braided suture) injected molded suture and followed by an extruded length of monofilament; a barbed coupling feature; and where the barbed coupling feature is a barbed fastener inserted longitudinally through a sock toe end of a braided suture and into the monofilament along the longitudinal axis thereof; a metallic titanium fastener; and metallic stainless steel fasteners. Moreover, as described above, where barbed coupling features are included, the barbed feature may be placed longitudinally or transversely into a receiving feature and, in certain embodiments, the barbs will be deformed to effect a permanent coupling.

In still other embodiments, a sleeve will be disposed circumferentially around a coupling that includes a barbed coupling where the sleeve provides a smooth external surface and prevents catching of the barbs on, for example, a surrounding tissue matrix. Moreover, combinations of the foregoing including, for example, a barbed coupling and a chemical adhesive, a barbed coupling and a laser welded bond, a barbed coupling and an ultrasonically welded bond, a barbed coupling at a thermally welded bond, a spherical coupling in any of the foregoing additional/supplemental bonds and a threaded coupling feature along with an ancillary or supplemental bond all will be advantageously employed in certain respective embodiments of the invention.

In certain embodiments, a suture according to principles of the invention will include a flat absorbable suture like a tape; absorbable and non-absorbable polymers; a fabric such as a polyester; and a coated suture having observable or absorbable coating. In certain embodiments, an internal reinforcing material will include a woven textile. In others a bioabsorbable material will be applied to a textile material by dipping or by coextrusion.

As noted above, certain kits and prepackaged assemblies will be made available within the scope of the invention including kits that contain a multipart suture and a separate or pre-connected needle; a multipart suture and a separate or pre-connected suture anchor; a multipart suture in any a variety of surgical instruments including forceps, scissors, an anchor insertion tool, or other surgical instruments. In still other embodiments, suture material will be provided including a large number of alternating suture portions of corresponding alternating characteristics all wound on a spool or other carrier device. Finally, in certain embodiments, a supply kit and apparatus will be provided that allow the preparation of a custom suture including a customized combination of suture portions of various length, physical properties and composition.

While the exemplary embodiments described above have been chosen primarily from the field of human surgical apparatus and techniques, one of skill in the art will appreciate that the principles of the invention are equally well applied, and that the benefits of the present invention are equally well realized in a wide variety of other areas of endeavor including, for example, veterinary medicine, horticulture, dentistry, etc. Further, while the invention has been described in detail in connection with the presently preferred embodiments, it should be readily understood that the invention is not limited to such disclosed embodiments. Rather, the invention can be modified to incorporate any number of variations, alterations, substitutions, or equivalent arrangements not heretofore described, but which are commensurate with the spirit and scope of the invention. Accordingly, the invention is not to be seen as limited by the foregoing description, but is only limited by the scope of the appended claims.

The invention claimed is:

1. A multicomponent suture comprising:
    a first suture portion having a first cross-sectional profile, said first suture portion including a first substantially bioabsorbable material; and
    a second suture portion having a second cross-sectional profile, said second suture portion including a first substantially non-bioabsorbable material, wherein said second suture portion includes a region having a flexible braided configuration comprising one or more of fibers, threads, and yarns that define apertures therebetween,
    wherein at least a portion of said first suture portion has a peripheral surface region configured to interact mechanically with said one or more of fibers, threads, and yarns such that said first and second suture portions are configured to be coupled to one another at respective mutually adjacent ends thereof so as to form an integrated suture having a first region that is substantially bioabsorbable and a second region that is substantially non-bioabsorbable.

2. The multicomponent suture of claim 1, wherein said first cross-sectional profile has a first aspect ratio, said first aspect ratio being substantially constant with respect to a longitudinal axis of said first suture portion, and wherein said—second—cross-sectional profile has a second aspect ratio, said second aspect ratio being substantially constant with respect to a longitudinal axis of said second suture portion.

3. The multicomponent suture of claim 2, wherein said first and second aspect ratios are related to one another by multiplicative factor of at least about 2.

4. The multicomponent suture of claim 2, wherein said first and second aspect ratios are related to one another by multiplicative factor of at least about 5.

5. The multicomponent suture of claim 2, wherein said first and second aspect ratios are related to one another by multiplicative factor of at least about 10.

6. The multicomponent suture of claim 2, where at least one of said first and second cross-sectional profiles is substantially circular.

7. The multicomponent suture of claim 2, where at least one of said first and second cross-sectional profiles is substantially elliptical.

8. The multicomponent suture of claim 2, where at least one of said first and second cross-sectional profiles is substantially rectangular.

9. The multicomponent suture of claim 1, wherein at least one of said first and second suture portions comprises a monofilament material.

10. The multicomponent suture of claim 1, wherein at least one of said first and second suture portions comprises a braided textile material.

11. The multicomponent suture of claim 1, wherein said first suture portion comprises a second substantially non-bioabsorbable material.

12. The multicomponent suture of claim 1, wherein said first suture portion exhibits a color that is substantially different from a color of said second suture portion.

13. The multicomponent suture of claim 1, wherein said first suture portion embodies a surface texture that is substantially different from a surface texture of said second suture portion.

14. A multicomponent suture assembly comprising:
a multicomponent suture comprising:
    a first suture portion having a first cross-sectional profile, said first suture portion including a first substantially bioabsorbable material; and
    a second suture portion having a second cross-sectional profile, said second suture portion including a first substantially non-bioabsorbable material, said first and second suture portions configured to be coupled to one another so as to form an integrated suture having a first region that is substantially bioabsorbable and a second region that is substantially non-bioabsorbable; and
an anchor configured to be coupled to the multicomponent suture such that the second suture portion is configured to be separated from the anchor after at least partial bioabsorption of the first suture portion, wherein said second suture portion includes a region having a flexible braided configuration comprising one or more of fibers, threads, and yarns that define apertures therebetween, and wherein at least a portion of said first suture portion has a peripheral surface region configured to interact mechanically with the one or more of fibers, threads, and yarns so as to couple the first and second suture portions to one another.

15. The multicomponent suture assembly of claim 14, wherein respective ends of the first suture portion are coupled to the second suture portion, the first suture portion forming a loop that is coupled to the anchor.

16. The multicomponent suture assembly of claim 14, wherein said first cross-sectional profile has a first aspect ratio, said first aspect ratio being substantially constant with respect to a longitudinal axis of said first suture portion, and wherein said cross-sectional profile has a second aspect ratio, said second aspect ratio being substantially constant with respect to a longitudinal axis of said second suture portion.

17. The multicomponent suture assembly of claim 14, wherein the anchor is configured to provide temporary stabilization of soft tissue via attachment of the multicomponent suture assembly to a bone tissue.

18. The multicomponent suture assembly of claim 17, wherein the second suture is configured to be disposed within the soft tissue.

\* \* \* \* \*